(12) United States Patent
Banfield et al.

(10) Patent No.: US 6,589,772 B1
(45) Date of Patent: Jul. 8, 2003

(54) ACIDOPHILE ARCHAEAL ORGANISM

(75) Inventors: Jillian F. Banfield, Madison, WI (US); Katrina J. Edwards, East Falmouth, MA (US); Philip L. Bond, Madison, WI (US); Thomas M. Gihring, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/515,996

(22) Filed: Feb. 29, 2000

(51) Int. Cl.[7] ............................. C12N 1/00; C07H 21/02
(52) U.S. Cl. ....................................... 435/243; 536/23.1
(58) Field of Search ........................... 435/243; 536/23.1

(56) References Cited

PUBLICATIONS

Edwards K. et al, Seasonal Variations in Microbial Populations and Environmental Conditions in an Extreme Acid Mine Drainage Environment. Applied and Environmental Microbiology, 1999, 65, 3627–3632.*

Edwards et al. Geomicrobiology of PYrite (FeS2) Dissolution: Case Study at Iron Mountain, California. Geomicrobiological Journal, 1999, 16, 155–179.*

Edwards K. et al. An Archeal Iron_Oxidizing Extreme Acidophile Important in Acid Mine Drainage, Science, 2000, 287, 1796–1799.*

McGuire M. et al, Kinetics, Surface Chemistry, and Structural Evolution of Microbially Mediated Sulfide Mineral Dissolution. Geochimica et Cosmochimica Acta, 2001, 65, 1243–1253.*

Edwards M. et al. A new look at microbial leaching patterns on sulfide minerals. FEMS Microbiology Ecology, 2001, 34, 197–206.*

* cited by examiner

Primary Examiner—Ponnathapu Achutamurthy
Assistant Examiner—Malgorzata A. Walicka
(74) Attorney, Agent, or Firm—Quarles & Brady LLP

(57) ABSTRACT

A new species of acidophilic microorganism has bee isolated from a acid mine drainage site. The organism is an archaea here given the tentative species designation *Ferroplasma acidarmanus* and the strain designation fer1. This organism is tolerant of extraordinary conditions of low pH and high metal concentrations.

2 Claims, 2 Drawing Sheets

ACIDOPHILE ARCHAEAL ORGANISM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to novel microorganisms and relates, in particular, to a novel archaeal microorganism which is an extremophile.

Microorganisms including both bacteria and archaeal species populate a wide variety of environmental niches throughout the planet earth. It is now known that microorganisms exist in the air, under the ocean, and even, perhaps, in subsurface geologic formations. The extent to which microorganisms have colonized and adapted for unique ecology niches is something that has only recently begun to be understood by microbiologists.

One category of microorganisms that has begun to receive some attention are those known as extremophiles. This term, perhaps not truly a rigorous scientific term, refers to microorganisms that have evolved to exist in ecological niches in which they are commonly exposed to environmental conditions which would have been thought, not very many years ago, to be too extreme to support living organisms. An example of entire ecological niches based on extremophiles has been discovered in sulfite metabolizing organisms which exist at the bottom of ocean trenches and derive their energy from geological rather than solar forces.

The modern biotechnology industry has come to understand that extremophiles represent a potential for biological prospecting for novel enzymes, sometimes referred to as extremozymes. Since a living organism is required to maintain its set of housekeeping enzymes in order to live and thrive, it naturally follows that an extremophile existing in a hostile environment has evolved enzymes which are capable of performing their appropriate catalytic activity under the conditions which the microorganism lives. If one looks at an organism which exists natively in a given environment that approximates the needs of an industrial process, it becomes possible to look for enzymes capable of catalyzing a needed reaction under the conditions existing in the corresponding industrial process. One well known example of this is the DNA polymerase from the organism *Thermus aquaticus*, which was originally isolated from a hot spring. The *Thermus aquaticus* DNA polymerase, referred to as Taq polymerase, is now widely used in the genetic engineering field, particularly in the performance of the PCR and DNA sequencing reactions, due to its thermal stability. The thermal stability of the polymerase was necessary in the native *Thermus aquaticus*, because its environment was a hot spring which natively exposed the host microorganism to exceedingly high temperatures.

Other extremophiles have been isolated which are heat tolerant thermophiles, cold tolerant psychrophiles, acid tolerant acidophiles, alkaline tolerant alkaliphiles, and salt tolerant halophiles.

One extremely hostile environment occurs where waste water pools emanate from iron mines. Iron is often found in geologic formations in the form of iron pyrite, and the interaction between materials such as sulfites, such as pyrite, water, microorganisms and air results in very acidic and metal rich waters. The accumulation of such acidic metal rich waters is accelerated by mining activities and results in a form of pollution acid mine drainage. However, sulfite solutions occur: naturally in the absence of mining, even though the human impact can enhance its accumulation.

Previous studies have suggested the role of some microorganisms in the processing and cycling of metals in acid mine drainage. In particular, the iron-oxidizing bacterium *Thiobacillus ferrooxidans* was thought to be the most important oxidizing species in acid mine drainage. However, later work has suggested that archaeal species may be more abundant than bacterial species in at least some important sites of acid mine drainage generation during at least the dry summer and fall months. Edwards et al., *Geomicrobiology Journal* 16: 155–179 (1979). To date the archaeal species present at such sites have not been characterized or cultured.

BRIEF SUMMARY OF THE INVENTION

It is reported here that a novel archaeal species has been identified in an acid mine drainage site. The isolate is a novel iron-oxidizing archaeal species that is capable of growth at extraordinarily low levels of pH, down to a pH of 0. The organism is abundant and even predominant in solutions of high conductivity and low pH. The organism is referred to here by a coined, but unofficial, species designation of *Ferroplasma acidarmanus*.

It is an object of the present invention to contribute to the knowledge of mankind the existence of a novel archaeal species that is more acid tolerant than other previously known species.

It is another object of the present invention to identify, culture and make available an organism which possesses, at a minimum, metal oxidizing and cell surface proteins and enzymes which have extreme tolerance to conditions of very low pH.

It is a further object of the present invention to describe a microorganism which is extremely tolerant of both low pH and high concentrations of.metals which might be toxic to less hardy strains or species, thus providing a biological platform for potential genetic engineering of organisms which can thrive in hostile environments.

Other objects, advantages and features of the present invention become apparent from the following specification when taken in conjunction with the accompanying drawings.

DETAILED DESCRIPTION OF THE INVENTION

Figure 1:
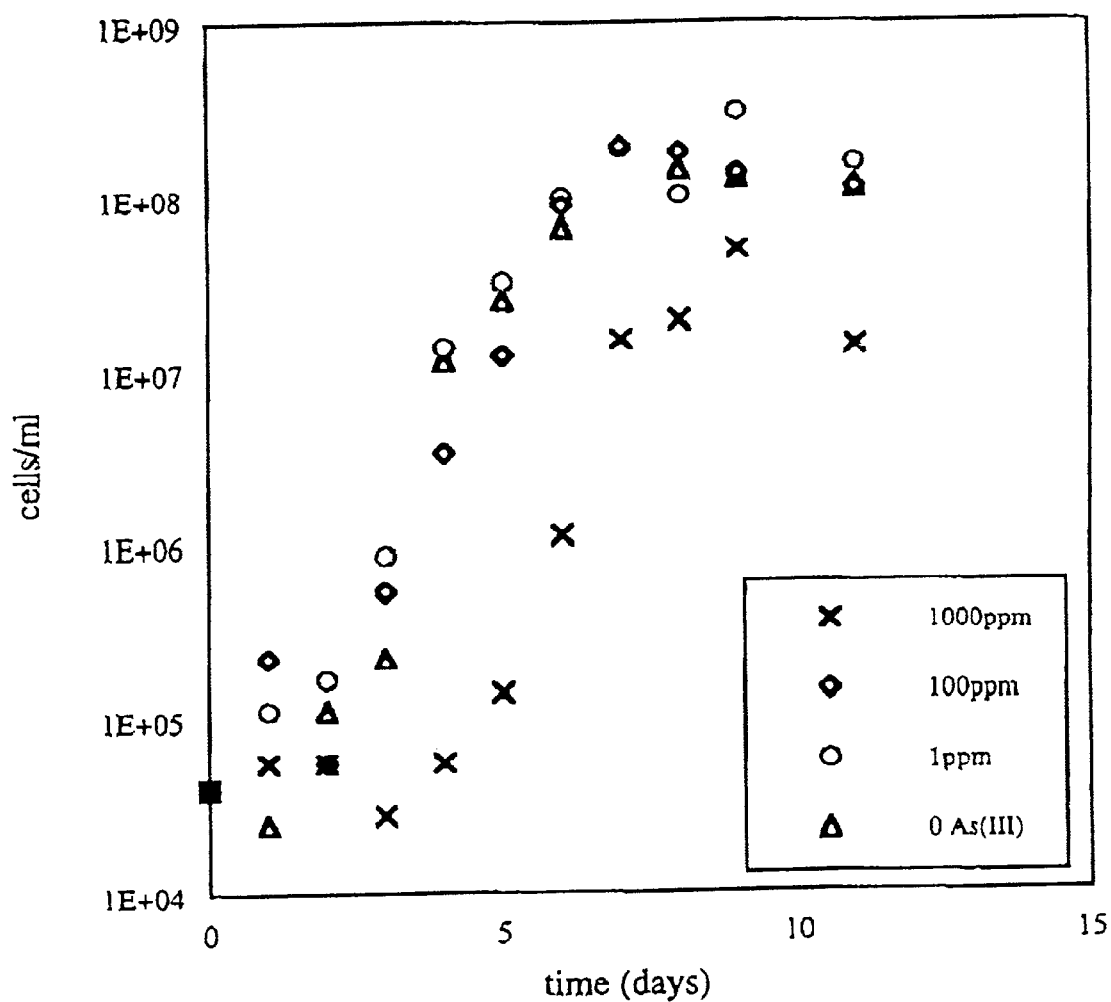
FIG. 1 and FIG. 2 are graphical representations of growth curves of cultures of the organism of the present invention under varying concentrations of arsenic.

A novel archaeal organism has been isolated from a high acid, high metal environment. The organism is novel to science and is here given the tentative species designation *Ferroplasma acidarmanus* and a strain designation fer1. It should be recognized that this species nomenclature is a tentative one coined by the inventors here and subject to modification by appropriate taxonomic authorities.

The organism fer1 is phylogenically very similar to *Ferroplasma acidophilum*, but is clearly physiologically distinct from that organism. Both fer1 and *F. acidophilum* require yeast extract for growth. However, fer1 is able to grow heterotrophically on yeast extract as its sole energy source, a capability which *F. acidophilum* lacks. The organism fer1 is robust and stable at pH ranges that are unprecedented to living organisms. fer1 is able to grow between a pH of 0 and a pH of 2.5 and achieves its growth optimal curve at a pH of about 1.2. By contrast, *F. acidophilum* grows over a more restricted pH range and has an optimal pH of about 1.7.

The initial culture of fer1 was isolated from sediment and slime samples from the Richmond Mine located in Iron Mountain, Calif. The organism was first cultured from a site in the mine known as a 5-way, which is a site about 500 meters inside the mountain situated within the remaining pyrite ore body and a junction between five tunnels. The conditions of the 5-way site include a temperature of about 30–50° C. with a pH between 0 and 1. The low pH supports very high concentrations of metals in solutions present at the site, as high as 111 grams of metal per liter, including copper, arsenic, cadmium and zinc. The specific conductance of the sample site solution was about 120 mS per cm.

In a sediment attached biofilm, collected from the 5-way, microbial communities were overwhelmingly dominated by *F. acidarmanus*, Approximately 85% of the biofilm population was *F. acidarmanus*. The remainder of the biofilm was composed of eukaryotic filaments. In essence, the entire prokaryotic community from the samples was *F. acidarmanus*. Hence, the species is a dominant microbial constituent of the. Richmond Five-Way.

Cultures taken from the solutions.at the site were grown as 37° C. in pH 1 medium as described in Edwards et al., *Appl. Environ. Microbiol.* 65, 3627–3632 (1999). Pyrite sediments were used as the energy source. Clone libraries were constructed for two of the enrichment cultures, and representative clones were sequenced. Results from the phylogenic analysis of the 16s rRNA gene sequence obtained indicated that a high proportion of the clones formed a monophyletic cluster with *Ferroplasma acidophiluum*, an acid-oxidizing autotrophic archaeon of the order Thermoplasmales. The Thermoplasmales are acidophilic archaea that lack cell wall or cell envelope. The isolate fer1 was isolated from an enrichment culture after serial dilution in pH 1.5 medium supplemented with 20 g/L $FeSO_4 \cdot 7H_2O$ and 0.02% yeast extract. The 16S rRNA gene was partially .sequenced and deposited to the GenBank data base with the accession number AF145441, also presented as SEQ ID NO1 below. Subsequent analysis confirmed that the isolate was a of the Ferroplasma genus but distinct from known species. The taxonomic designation *Ferroplasma acidarmanus* was coined for this proposed new species.

Microbial populations at acid mine drainage sites underground are typically poorly studied relative to those populations which can be found in runoff waters, due to the greater difficulty associated with sampling.the often disused and hazardous sites in the subsurface. At the Richmond Five-Way Mine in Iron Mountain, Calif., it appears that the dominant archaeal species is *F. acidarmanus* and it appears to be an abundant iron oxidizing species at the site. These samples were taken from a site where possible the lowest naturally occurring pH conditions, that have yet been identified on the planet, exist. In the subterranean formations in which the organism is prevalent, the mountain has been extensively mined resulting in a network of tunnels and stopes throughout a massive sulfide ore body. The mining has enhanced the flow of water and air through the ore body and increased the rate of dissolution of pyrite. The dissolution of the sulfide bearing mineral is enhanced by the acidophilic organisms. Typical conditions of pyrite dissolution in the mine are an ambient temperature of 30 to 50° C., a pH of 0.5 to 0.9, iron concentration in the range of tens to hundreds of grams per liter and a conductivity in the range of 50 to 125 mS per centimeter. The microbial growth within the tunnels is obvious on a macroscopic scale in the forms of slimes and streamers. Microscopic examination reveals individual cells and biofilms attached to the pyrite.

Using a fluorescently labeled oligonucleotide probe and DNA to RNA hybridization, described below in the examples, it has been found that the fer1 organism is a major proportion of microbial communities in prominent acid producing localities within the mine.

A sample of the fer1 culture has been deposited under the terms of the Budapest Treaty with the American. Type Culture Collection in Manassass, Va. as ATCC accession number PTA-1417 on Feb. 23, 2000.

Figure 2:
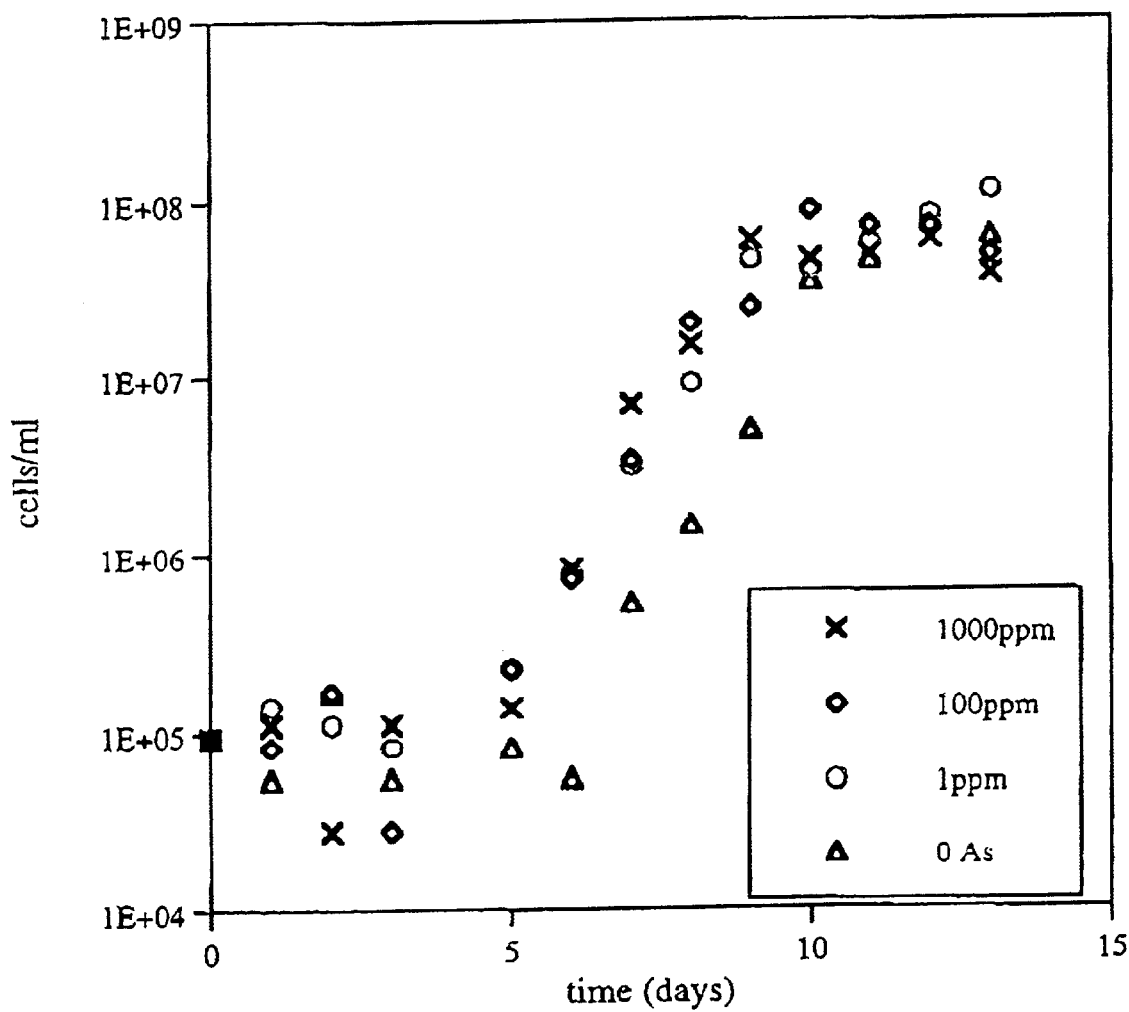

To further characterize the isolate designated *Ferroplasma acidophilum*, some characteristics of the strain fer1 were determined and compared to the bioleaching reactor isolate *Ferroplasma acidophilum*. Both organisms are iron oxidizing, pleomorphic acidophiles. However an analysis of the 16S rRNA gene sequences of the two Ferroplasma species finds great similarities even though there are substantial physiological and metabolic differences that differentiate the species. fer1 has more extreme pH tolerance, higher temperature optimum and grown heterotrophically as well as mixotrophically. fer1 is able to grow heterotrophically on yeast extract as a sole energy source, while *F. acidophilum* cannot. fer1 also exhibits growth rates, at its optimal pH, about 3 times that of *F. acidophilum* at its optimum pH. The metal tolerance of fer1 is best illustrated by FIG. 1 and 2, which are graphical representations of growth curves for the culture of the organism under varying concentrations of arsenic.

TABLE 1

Comparison of lay characteristics of isolate *Ferroplasma acidarmanus* fer1 and *Ferroplasma acidiphilum*[a]

|  | *Ferroplasma acidarmanus* Fer1 | *Ferroplasma acidiphilum*[b] |
| --- | --- | --- |
| Morphology | Pleomorphic | Pleomorphic |
| Autotrophy | Nd[c] | + |
| Heterotrophy | + | − |
| $Fe^{2+}$ oxidation | + | + |
| Aerobic growth | + | + |
| T optimum ° C. | 45 | 35 |
| T range ° C. | Nd | 15–45 |
| pH optimum | 1.2 | 1.7 |
| PH range | 0.0–3.0 | 1.3–2.2 |

[a]+, positive growth or reaction; − negative growth or reaction
[b]A bioleaching reactor isolate, data from Golyshina et al., submitted to CJSB
[c]Nd, not determined Another unique trait of this organism is its high tolerance for concentrations of arsenic. Cultures of *F. acidarmanus* can grow on many different sulfite ores including pyrite, marcasite and arsenopyrite. In part because of this trait, the ability of the organism to tolerate arsenic concentrations was examined. Cultures were grown in media containing additions of 0, 1 , 100 and 1000 parts per million arsenic or arsenate, and none of the media adversely affected the growth rates of the cultures. It is therefore expected that the organism carries genes for arsenic resistance which allows the organism to function normally in an otherwise toxic environment.

This new species of organism has several potential industrial uses. The process of bioleaching involves the same processes that occur in the generation of acid mine drainage. There are several studies demonstrating that the bioleaching of low grade metal ores has become economically feasible. Both *F. acidarmanus* as a species and fer1 as a strain are strong candidate strains for this process.

It is also envisioned that this organism is a fertile source for the identification and cloning of acid tolerant enzymes. While the intra-cellular pH of the organism is likely to be somewhat moderated from the high-acid environment in which it lives at least all of the proteins natively made by the organism which extend to or through the cell membrane must by definition be highly acid tolerant. It is also possible that the internal basic biochemical enzymes of the organism will prove to be more acid tolerant than comparable enzymes from other species. Such acid tolerant enzymes would have uses in industrial processes, particularly ones involving metal oxidation, but could also have uses in medicines and food preparation.

One of the first targets of enzyme searching from the organism is for the enzyme responsible for iron oxidation.

The fer1 organism contributes to acid mine drainage by catalysis of the following reaction:

$$FeS_2 + 14\ Fe^{3+} + 8\ H_2O \rightarrow 15Fe^{2+} + SO_4^{2-} + H^+$$

This is one of the key energy metabolizing pathways for the organism. A 14 kD protein has been identified from the organism which is expressed preferentially by the organism under conditions when the organism is actively oxidizing iron. The protein has been isolated and its N-terminal amino acid sequence has been derived. The first twenty amino acids of that sequence are set forth as SEQ ID NO:2 below. This information characterizes the enzyme such that one of skill in the art can recover the DNA coding sequence for this enzyme, thus permitting genes for the enzyme to be reconstructed into any suitable host. Thus, the enzyme can be produced for use alone, as; an iron oxidizing enzyme, or the gene encoding the enzyme can be placed into a host tailored for enhanced bioleaching performance.

It is to be understood that the present invention is not limited to the particular embodiments described above, but embraces all such modifications and changes thereto as come within the scope of the following claims.

We claim:

1. An isolated culture of *Ferroplasma acidarmanus*, strain fer1.

2. An isolated culture of the archaeal organism *Ferroplasma acidarmanus*, wherein the 16S rDNA of the organism has the sequence of SEQ ID NO:1.

* * * * *

UNITED STATES PATENT AND TRADEMARK OFFICE
CERTIFICATE OF CORRECTION

PATENT NO.    : 6,589,772 B1
DATED         : July 8, 2003
INVENTOR(S)   : Jillian F. Banfield et al.

It is certified that error appears in the above-identified patent and that said Letters Patent is hereby corrected as shown below:

<u>Title page,</u>
Item [*] Notice, please delete the entire paragraph and insert therefor the following:
-- This invention was made with United States government support awarded by the following agencies: NSF 9807598. The United States has certain rights in this invention. --

Signed and Sealed this

Seventeenth Day of August, 2004

JON W. DUDAS
*Acting Director of the United States Patent and Trademark Office*

SEQUENCE LISTING

<160> NUMBER OF SEQ ID NOS: 2

<210> SEQ ID NO 1
<211> LENGTH: 849
<212> TYPE: DNA
<213> ORGANISM: Ferroplasma Acidarmanus
<220> FEATURE:
<221> NAME/KEY: unsure
<222> LOCATION: (342)
<223> OTHER INFORMATION: unsure
<220> FEATURE:
<221> NAME/KEY: unsure
<222> LOCATION: (371)
<223> OTHER INFORMATION: unsure

<400> SEQUENCE: 1

```
ttttgtaaat cttcagataa agcctgaagc ttaactccag aaagtctgaa gagactgcaa      60
gacttgagat cgggtgaggt taaacgtact ttcagggtag gggtaaaatc ctgtaatccc     120
ggaaggacga ccagtggcga aagcgtttaa ctagaacgaa tctgacggta aggaacgaag     180
gctagggtag caaaccggat tagatacccg ggtagtccta gctgtaaaca ttgcccattt     240
gatgttgctt ttccgttgag ggaaggcagt gtcggagcga aggtgttaaa tgggccgctg     300
ggaagtatgg tcgcaagact gaaacttaaa ggaattggcg gnggagcacc gcaacgggag     360
gaatgtgcgg nttaattgga ttcaacgccg gaaaactcac cgggaacgac ctgtgcatga     420
gagtcaacct gacgagctta ctcgatagca gagaggtggt gcatggccgt cgtcagctcg     480
taccgtaggg cgttcacttt aagtgtgata acgagcgaga cccacatctt taattgcaaa     540
tgtatatgag aatatgcatg cactttagag aaaccgccag cgctaagctg gaggaaggag     600
tggtcgacgg caggtcagta cgccccgaat ttcccgggct acacgcgcat tacaaagaac     660
gggacaatac gttgcaacct cgaaagagga agctaatcgc gaaacccgtc catagttagg     720
attgagggct gtaactcgcc ctcatgaatc tggattccgt agtaatcgcg ggtcaacaac     780
ccgcggtgaa catgcccctg ctccttgcac acaccgcccg tcaaaccatc cgagttggtg     840
ttggatggc                                                            849
```

-continued

```
<210> SEQ ID NO 2
<211> LENGTH: 20
<212> TYPE: PRT
<213> ORGANISM: Ferroplasma Acidarmanus

<400> SEQUENCE: 2

Thr Glu Glu Asn Lys Glu Asn Glu Thr Thr Glu Asp Glu Asn Val Val
  1               5                  10                  15

Arg Lys Thr Ile
            20
```